United States Patent [19]

Nunan et al.

[11] Patent Number: 4,736,052
[45] Date of Patent: Apr. 5, 1988

[54] PURIFICATION OF DIARYL ALKYLPHOSPHONATE REACTION MIXTURE

[75] Inventors: R. Anthony Nunan, Yonkers; John Tomko, Dobbs Ferry; Edward D. Weil; George C. Ciomo, both of Hastings-on-Hudson, all of N.Y.

[73] Assignee: Stauffer Chemical Company, Westport, Conn.

[21] Appl. No.: 11,572

[22] Filed: Feb. 6, 1987

[51] Int. Cl.$^4$ .............................................. C07F 9/40
[52] U.S. Cl. ................................................ 558/146
[58] Field of Search .................. 558/146, 122, 215

[56] References Cited

U.S. PATENT DOCUMENTS

| | | | |
|---|---|---|---|
| 3,384,684 | 5/1968 | Boschan et al. | 558/215 |
| 3,408,428 | 10/1968 | Boschan et al. | 558/215 |
| 4,152,373 | 5/1979 | Honig et al. | 558/122 |
| 4,377,537 | 3/1983 | Block et al. | 558/122 |

OTHER PUBLICATIONS

Chemical Abstracts, vol. 91, 39645t (1979).

*Primary Examiner*—Anton H. Sutto
*Attorney, Agent, or Firm*—Richard P. Fennelly

[57] ABSTRACT

The reaction residue containing diaryl alkylphosphonate resulting from the reaction of triaryl phosphite and alcohol in the presence of a rearrangement catalyst is treated by optionally, and preferably, stripping phenol by-product therefrom, optionally, and then treating the residue with aqueous dilute acid to convert unreacted triaryl phosphite reagent to diaryl phosphite and remove it as an aqueous layer, and then treating the remaining residue with an aqueous base to yield a water phase containing the unwanted diarylphosphite by-product and an organic phase containing the desired diaryl alkylphosphonate, with subsequent removal of the water phase, prior to subsequent distillation of the remaining organic phase residue to remove purified diaryl alkylphosphonate therefrom.

6 Claims, No Drawings

PURIFICATION OF DIARYL ALKYLPHOSPHONATE REACTION MIXTURE

BACKGROUND OF THE PRESENT INVENTION

1. Field of the Present Invention

The present invention is directed to a purification technique for treating the reaction mixture comprising a diaryl alkylphosphonate.

2. Description of the Prior Art

Diaryl alkylphosphonates can be prepared by the reaction of an alcohol, such as methanol, with an appropriate triaryl phosphite, for example triphenyl phosphite, in the presence of a rearrangement catalyst. Suitable rearrangement catalysts include strong acids, such as paratoluenesulfonic acid, perfluorooctanesulfonic acid, $F_3CCO_2H$, or alkyl halides, such as methyl iodide. Examples of processes which use such an approach include: German Patent Application No. 2,747,554; M. L. Honig et al., Journal of Organic Chemistry, Vol. 42, 379 (1977); and U.S. Pat. No. 4,152,373 to M. L. Honig et al. The triaryl phosphite that can be used in such a procedure includes aryl radicals containing from about 6 to about 14 carbon atoms, inclusive. Illustrative groups of this type include phenyl, naphthyl, anthracyl, phenanthryl, and the like. The aryl radicals can be either substituted with non-interfering substituents such as alkyl, phenyl, chloro, bromo, alkoxy, aryloxy, alkylthio, arylthio, cyano, nitro and/or hydroxy, or they can be unsubstituted. The alcohol which is used is preferably a lower alkyl (e.g., $C_1$ to $C_4$) alcohol with methanol being representative. The weight ratio of the phosphite to the alcohol can range from about 2:1 to about 1:2 parts by weight. However, it is preferable to employ a slight excess of the alcohol over the stoichiometric amount needed. Temperatures used in the reaction can range from about 150° C. to about 300° C. The catalytic amount of rearrangement catalyst can range from about 0.1% to about 10% by weight, with ranges of from about 0.5% to about 5% by weight being generally employed.

It has been found that when the above type of reaction is conducted, the later distillation of the desired product, diaryl alkylphosphonate, from the reaction mixture is greatly complicated by the additional presence, for example, in the reaction residue of unreacted triaryl phosphite starting material and undesired by-product diaryl phosphite. Moisture can cause the triaryl phosphite starting material to act to form the unwanted diaryl phosphite by-product. The diaryl phosphite by-product is believed to be the main cause of unwanted color formation in the reaction residue, smoking of the reaction residue, and the forming of unwanted pyrophoric moieties in the reaction residue when the residue is subjected to distillation to remove and recover the desired product from the reaction mixture. At the start of the distillation procedure, the presence of such unwanted by-products as diaryl phosphite and of unreacted triaryl phosphite is of much less a problem than later on in the distillation procedure. At a later point in the distillation procedure, however, the relative concentration of the diaryl phosphite, for example, and triaryl phosphite in the residue is greatly increased as the desired product is removed from the residue. At some point in the distillation problems can arise due to color formation, smoking, or the formation of pyrophoric substances. The present invention provides a means for the removal, for example, of undesired by-product, e.g. diaryl phosphite by-product and unreacted triaryl phosphite, from the above-mentioned type of reaction residue.

DESCRIPTION OF THE PRESENT INVENTION

The reaction residue resulting from the reaction of triaryl phosphite with alcohol in the presence of a rearrangement catalyst comprises a predominant amount of the desired diaryl alkylphosphonate, phenol by-product, unreacted triaryl phosphite starting material, and undesired diphenyl phosphite. The amount of the diaryl alkylphosphonate in the reaction residue can be in the neighborhood of only about 60–65% due to the presence of undesired reaction by-products and unreacted reagents.

An optional, but preferred procedure for practice of the present invention involves a prestripping procedure which results in the removal of unwanted phenol by-product from the reaction residue. This step avoids undesired emulsion formation and material loss during the procedure. This prestripping procedure is shown in the aforementioned U.S. Pat. No. 4,152,373 to M. L. Honig et al. and involves the use of temperatures of up to about 180° C., for example, under subatmosphere pressure to result in the removal of phenol from the reaction mixture prior to the intended distillation and recovery of the undesired diaryl alkylphosphonate product from the residue that remains.

A subsequent treatment step, if the preferred prestripping procedure is used in conjunction with the present invention, is the use of an aqueous solution of a dilute, low boiling acid, such as hydrochloric acid, to further hydrolyze diaryl phosphite species to phenols and either monoaryl phosphite or phosphorous acid (or both), either or both of which can be washed out, in part, with the aqueous acid and, in part, with the subsequent water and alkaline washes. The aforesaid appropriate conversion and removal of these species could be obtained by the use of water alone, but it has been found that this is too slow. The rate of conversion and removal is greatly enhanced by the use of a dilute acid solution, such as hydrochloric acid. The water layer containing the undesired materials is removed and discarded.

The next step in the present invention involves the washing of the organic reaction residue containing the diaryl alkylphosphonate, diphenyl phosphite, and phenol (if any of the latter is present) with an aqueous base to neutralize the diphenyl phosphite and cause the unwanted residue to be present in the resulting water phase. The formation of the undesired water-soluble species in the water layer from the organic phase containing the diaryl alkylphosphonate allows for the subsequent distillation of the organic phase without the unwanted color formation, smoking, and/or formation of pyrophoric species that existed in regard to the prior art procedures.

The foregoing invention is further illustrated in the attached Examples which illustrate certain embodiments of the present invention.

EXAMPLE 1

This illustrates a preferred embodiment for practice of the present invention.

A 100-gallon reactor heated with mineral oil in a jacket and equipped with an agitator, a glass column and a condenser, was purged with nitrogen and triphenyl phosphite (528 lbs.) was added to it. The reactor unit was set for total reflux and the triphenyl phosphite was heated to 227° C. When at this temperature, the nitrogen purge was stopped, cold water was circulated through the condenser, and 58 lbs. of a methanol/-methyl iodide mixture formed by mixing 66 lbs. of methanol with 1.5 lbs. of methyl iodide was fed under 3 psig nitrogen pressure through a dip tube from a 15-gallon stainless steel container at an initial rate of about 7 lbs./hr. over a period of about 8 hours. The reactor temperature was kept below about 230° C. during the reaction. The reactor content was allowed to cool overnight.

In order to drive the reaction to substantial completion, the reaction mixture was heated back to 227° C. and 2 lbs. of a supplemental methanol/methyl iodide mixture was added to the reactor vessel at a rate of 0.5 lbs./hr., reducing the triphenyl phosphite content of the reaction mixture from 0.75% to 0.08%.

The reactor, after completion of the reaction, was then set for distillation with a second reactor being used as the receiver. Vacuum was applied gently to first remove unreacted methanol and anisole by-product with some foaming of the reaction residue in the reactor. When the foaming subsided, heating was begun and a 10-15 mm Hg vacuum was reached. At this point, warm water cooling at 49° C. was applied to the condenser and the receiver. Phenol by-product was distilled up to a reactor temperature of 149° C., a vapor temperature of 121° C., and a vacuum of 10 mm Hg. The crude diphenyl methylphosphonate reaction mixture in the 100-gallon reactor was then cooled to 49° C. and the phenol collected in the receiver was drained. The phenol content of the reaction mixture after this operation was about 3.2% phenol.

Cold water (40 gallons) was then added to the crude reaction mixture in the reactor and 5 lbs. of a concentrated (30-32%) hydrochloric acid solution. The mixture was agitated for 30 minutes, and then the organic and aqueous layers were allowed to separate. Each was placed in separate drums.

The organic layer from the preceding step was then recharged into the reactor and 40 gallons of water was added to it. The agitator was turned on and 25 lbs. of sodium bicarbonate was added to it in small portions with intensive foaming being generated. The agitation was applied for 30 minutes and the respective organic and aqueous layers were allowed to separate for one hour. Each respective layer (aqueous and organic) was then placed in separate drums.

The treatment with sodium bicarbonate was repeated after the organic layer had been reintroduced to the reactor and the resulting organic and aqueous layers are separately placed in drums. The organic layer was then reintroduced to the reactor.

With the acid number of the washed diphenyl methylphosphonate under 0.1 mg KOH/gm, full vacuum was applied to the reactor and heating was begun. A forecut of water and phenol was collected in the receiver until a reactor pot temperature of 171° C. and a vapor temperature of 143° C. was reached at 10 mm Hg in the reactor. At this point, the receiver was emptied and distillation of diphenyl methylphosphonate product was allowed to proceed at reaction pot temperature of 204° C.; a vapor temperature of 193° C., and a pressure of 10 mm Hg. The distilled product was then collected having an assay of 97% and a phenol content of 2.5%.

The following output material balance was achieved:

| Component | Lbs. |
| --- | --- |
| Phenol By-product | 126.0 |
| Forecuts From Distillation | 35.0 |
| Distilled Phosphonate | 337.0 |
| Residues | 40.0 |
| Losses | 50.0 |

EXAMPLE 2

Crude diphenyl methylphosphonate (acidity: 18.3 mg KOH/gm) (127 gm) was first washed twice with 200 cc aliquots of 0.1N hydrochloric acid and then three times with 200 cc aliquots of saturated sodium bicarbonate until carbon dioxide evolution was no longer evident. Following these procedures, the organic layer that remained was washed twice with 200 cc aliquots of water. The washed organic layer, after separation, was then stripped to 40° C. and 10 mm Hg. The weight of purified product was 92.21 gm with an acidity of 0.6 mg KOH/gm.

EXAMPLE 3

Another 382.8 gm batch of crude diphenyl methylphosphonate (acidity: 3.82 mg KOH/gm) was washed as follows:

(a) 1×400 cc of 0.1N hydrochloric acid
(b) 1×200 cc of 0.1N hydrochloric acid
(c) 1×300 cc of water
(d) 4×300 cc of saturated sodium bicarbonate
(e) 3×300 cc of water After the above-described washing procedure, the washed and separated organic was stripped to 40° C. and 10 mm Hg for 1.5 hours and then to 40° C. and 0.5 mm Hg until a constant weight was achieved.

The yield of final stripped product was 319.82 gm with an acidity of 0.5 mg KOH/gm.

The foregoing Examples are presented for illustrative purposes only and should not be construed in a limiting sense. The scope of protection that is sought is set forth in the claims which follow.

We claim:

1. A process for the purification of a diaryl alkylphosphonate reaction residue formed by the reaction of triaryl phosphite and alcohol in the presence of a rearrangement catalyst which comprises treating the reaction residue first with an aqueous solution of a dilute acid with removal of the resulting aqueous layer and the subsequent treatment of the reaction residue with an aqueous solution of base with removal of the resulting aqueous layer prior to subsequent distillation of the residue which remains to remove purified diaryl alkylphosphonate therefrom.

2. A process as claimed in claim 1 wherein the acid which is used is hydrochloric acid.

3. A process as claimed in claim 1 wherein the alcohol is a $C_1$-$C_4$ alkyl alcohol.

4. A process as claimed in claim 1 wherein the diaryl alkylphosphonate is diphenyl methylphosphonate.

5. A process as claimed in claim 1 wherein the acid is hydrochloric acid and the alcohol is a $C_1$-$C_4$ alkyl alcohol.

6. A process as claimed in claim 5 wherein the diaryl alkylphosphonate is diphenyl methylphosphonate.

* * * * *